United States Patent [19]

George et al.

[11] Patent Number: 4,650,796
[45] Date of Patent: Mar. 17, 1987

[54] 3-ACYLAMINOMETHYLIMIDAZO[1,2-A]PYRIDINE DERIVATIVES AND PHARMACEUTICAL COMPOSITIONS CONTAINING THEM

[75] Inventors: Pascal George, Vitry S/Seine, Belgium; Claude Giron, Antony, France

[73] Assignee: Synthelabo, Paris, France

[21] Appl. No.: 826,966

[22] Filed: Feb. 7, 1986

Related U.S. Application Data

[63] Continuation-in-part of Ser. No. 763,008, Aug. 6, 1985, abandoned.

[30] Foreign Application Priority Data

Aug. 7, 1984 [FR] France .................. 84 12447

[51] Int. Cl.$^4$ .................. A61K 31/44; C07D 471/04
[52] U.S. Cl. .................. 514/213; 514/300; 546/121; 540/524
[58] Field of Search .................. 546/121; 260/244.4; 514/213, 300

[56] References Cited

FOREIGN PATENT DOCUMENTS 1076089 7/1967 United Kingdom .................. 546/121

Primary Examiner—Henry R. Jiles
Assistant Examiner—Bernard I. Dentz
Attorney, Agent, or Firm—Wegner & Bretschneider

[57] ABSTRACT

Compounds which are imidazo[1,2-a]pyridine derivatives of general formula (I)

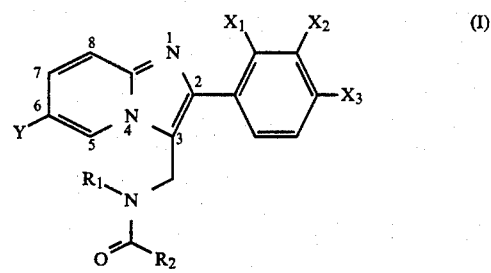

in which each of $X_1$, $X_2$, $X_3$, independently of each other, is hydrogen, halogen, $C_1$-$C_4$ alkyl, methoxy, methylthio, ethylthio, methylsulphonyl, nitro, amino, methylamino, dimethylamino, acetylamino or diacethylamino, Y is hydrogen, chlorine or methyl, $R_1$ is hydrogen, $C_1$-$C_4$ alkyl or benzyl, $R_2$ is $C_1$-$C_6$ alkyl, cyclohexyl, trichloromethyl, 1-propenyl, allyl, phenyl, 4-chlorophenyl or benzyl, or $R_1$ and $R_2$ together represent a divalent $C_3$-$C_5$ alipathic group and their pharmaceutically acceptable acid salts have anxiolytic, sleep-inducing, hypnotic, anticonvulsant, analgesic and anti-ulcer properties.

7 Claims, No Drawings

3-ACYLAMINOMETHYLIMIDAZO[1,2-A]PYRIDINE DERIVATIVES AND PHARMACEUTICAL COMPOSITIONS CONTAINING THEM

This application is a continuation-in-part of U.S. Ser. No. 763,008, filed Aug. 6, 1985 now abandoned.

The present invention relates to 3-acylaminomethylimidazo[1,2-a]pyridine derivatives.

According to the invention there are provided compounds which are imidazo[1,2-a]pyridine derivatives of the general formula (I)

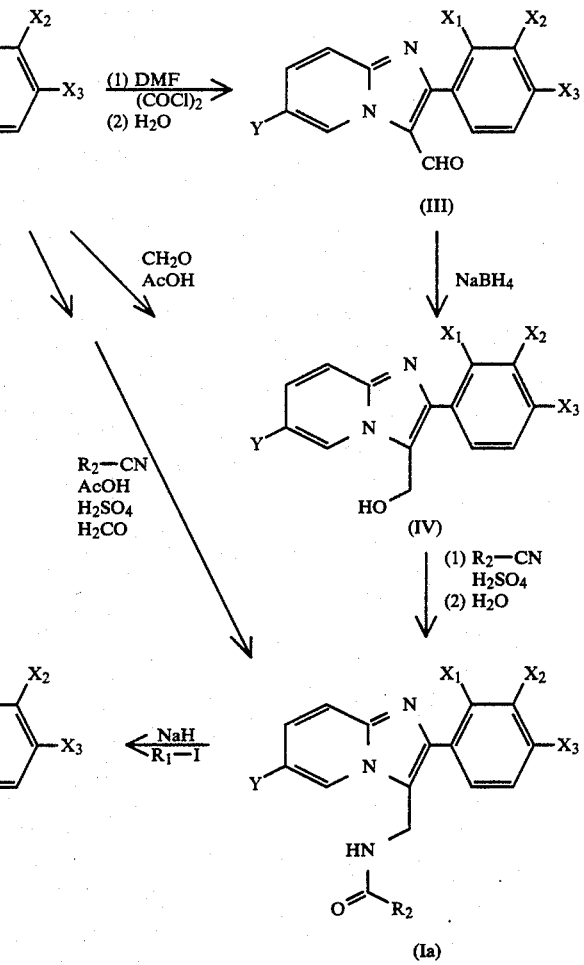

in which each of $X_1$, $X_2$, $X_3$, independently of each other, is hydrogen, halogen, $C_1$-$C_4$ alkyl, methoxy, methylthio, ethylthio, methylsulphonyl, nitro, amino, methylamino, dimethylamino, acetylamino or diacetylamino, Y is hydrogen, chlorine or methyl, $R_1$ is hydrogen, $C_1$-$C_4$ alkyl or benzyl, $R_2$ is $C_1$-$C_6$ alkyl, cyclohexyl, trichloromethyl, 1-propenyl, allyl, phenyl, 4-chlorophenyl or benzyl, or $R_1$ and $R_2$ together represent a divalent $C_3$-$C_5$ aliphatic group, and their pharmaceutically acceptable acid salts.

The preferred compounds are those of formule (I) in which at least one $X_1$, $X_2$, $X_3$ is methyl, chlorine, methoxy, methylthio, Y is hydrogen, chlorine, or methyl, $R_1$ is hydrogen or methyl and $R_2$ is propyl or isobutyl.

The amides of formula (I) can be prepared according to the scheme illustrated below.

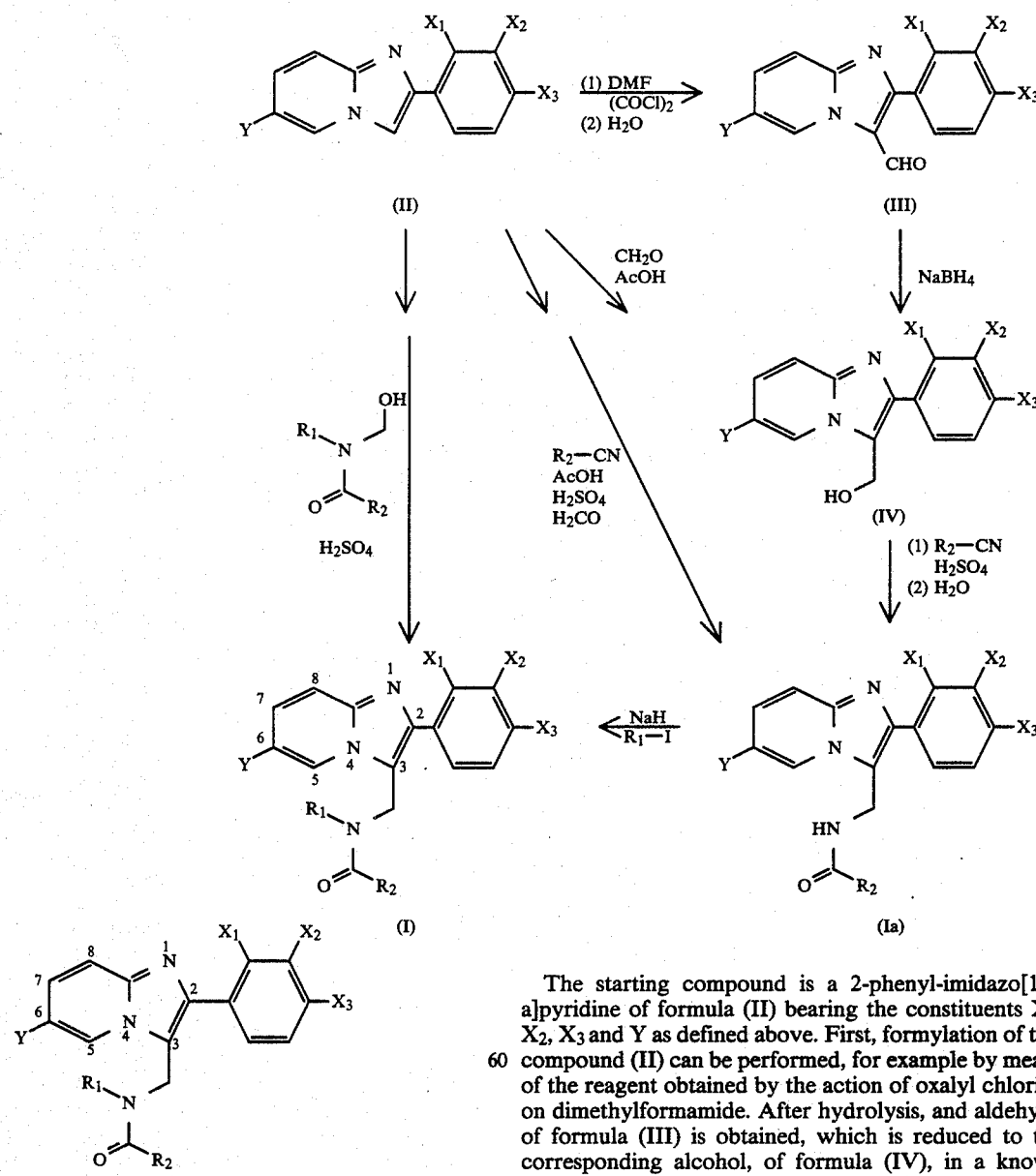

The starting compound is a 2-phenyl-imidazo[1,2-a]pyridine of formula (II) bearing the constituents $X_1$, $X_2$, $X_3$ and Y as defined above. First, formylation of this compound (II) can be performed, for example by means of the reagent obtained by the action of oxalyl chloride on dimethylformamide. After hydrolysis, and aldehyde of formula (III) is obtained, which is reduced to the corresponding alcohol, of formula (IV), in a known manner, for example by the action of an alkali metal borohydride. The alcohol (IV) can also be obtained by direct hydroxymethylation of the imidazopyridine (II) using aqueous formaldehyde in acetic acid.

This alcohol (IV) is then reacted with a nitrile of formula R$_2$—CN, suitably in sulphuric medium. After hydrolysis, an amide of formula (Ia) is obtained, in which the substituent R$_1$ is necessarily hydrogen. If desired, this amide can be alkylated or benzylated in a known manner, for example with an iodide of formula R$_1$—I in which R$_1$ is C$_1$-C$_4$ alkyl or benzyl in the presence of sodium hydride, to give an amide of formula (I) in which R$_1$ is C$_1$-C$_4$ alkyl or benzyl. Amides of formula (I) can also be prepared in a single stage, by reacting the starting compound (II) with an amide of formula

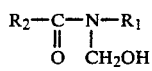

in which R$_1$ and R$_2$ are as defined above. The reaction is suitably performed at room temperature, in the presence of concentrated sulphuric acid and optionally with a cosolvent such as glacial acetic acid.

Finally, amides of formula (Ia) can also be prepared by reacting the starting compound (II) with a nitrile of formula R$_2$—CN and paraformaldehyde, suitably in the hot state, in acetic acid medium and in the presence of sulphuric acid. Compound (Ia) obtained after hydrolysis can then, if so desired, be alkylated or benzylated as described above.

An amide of formula (I) produced by any of these methods can be converted in manner known per se into an acid addition salt.

The Examples which follow illustrate the preparation of some compounds according to the invention. The structures of the compounds were confirmed by microanalysis and IR and NMR spectra.

EXAMPLE 1

2-(4-Chlorophenyl)-3-pentanoylaminomethyl-6-methylimidazo[1,2-a]pyridine.

(a) In a round-bottomed flask maintained at between −30° and −40° C. and containing 150 ml of dimethylformamide, 63 g, equivalent to 43 ml (0.5 mol), of oxalyl chloride are introduced dropwise while stirring. The mixture is allowed to return to room temperature, a suspension of 40 g (0.165 mol) of 2-(4-chlorophenyl)-6-methylimidazo[1,2-a]pyridine in 150 ml of dimethylformamide is then added, and stirring is continued for 24 hours. The precipitate is separated by filtration and suspended in 1 liter of water, and 350 ml of ammonia solution are added while this suspension is stirred.

The mixture is extracted with methylene chloride, and the organic phase is separated, washed with water, dried over magnesium sulphate and evaporated. The residue is rinsed with ether and recrystallised in methanol. A white solid is obtained. M.p.=175°-176° C.

(b) A suspension is prepared of 40 g (0.148 mol) of the aldehyde obtained above in 500 ml of methanol, and a solution of 3.5 g of sodium borohydride in 15 ml of water is added rapidly. Heating of the mixture is noted, and the strong evolution of a gas.

The mixture is stirred for 24 hours and then evaporated to dryness, the residue is taken up in water, the pH adjusted to 8 with dilute hydrochloric acid, and the precipitate filtered, washed and dried. M.p.=214°-215° C.

(c) In a round-bottomed flask, 6.12 ml (0.0588 mol) of valeronitrile and 32 ml of sulphuric acid are introduced. The mixture is stirred, 8 g (0.0293 mol) of the alcohol prepared above are added thereto in small portions, and stirring is continued until dissolution is complete.

Iced water is then added, followed by ammonia solution until pH >7, and the mixture is extracted with methylene chloride. The organic phase is separated, washed, dried and evaporated. The residue is washed with ether and then purified by chromatography on silica, eluting with a 96:4 methylene chloride/methanol mixture. The final product melts at 172°-173° C.

EXAMPLE 2

2-(4-Chlorophenyl)-3-[N-(methyl)pentanoylaminomethyl]-6-methylimidazo[1,2-a]pyridine.

In a 150 ml round-bottomed flask, 1.27 g (0.0264 mol) of sodium hydride at 50% strength in oil is introduced and washed twice with pentane, and 30 ml of tetrahydrofuran and 1.5 ml of dimethylformamide are added.

4.7 g (0.0132 mol) of the amide obtained according to Example 1, dissolved in 150 ml of tetrahydrofuran, are then introduced under argon, followed by 1.64 ml (0.0264 mol) of iodomethane.

The evolution of a gas is noted. The progress of the reaction is followed by thin layer chromatography on silica. When there is no longer any starting material, methanol is added to destroy the excess sodium hydride. The mixture is evaporated to dryness and taken up in water and methylene chloride, and the organic phase is separated, washed with water, dried and evaporated. The residue is taken up with ether, and then purified by chromatography on the silica column, eluting with a 97:3 methylene chloride/methanol mixture. The final product melts at 158°-160° C.

EXAMPLE 3

2-(4-Chlorophenyl)-3-(2-methylpropanoylaminomethyl)-6-methylimidazo[1,2-a]pyridine.

In a 150 ml round-bottomed flask, 1.5 g (0.05 mol) of paraformaldehyde, 50 ml of acetic acid, 4.55 ml (0.05 mol) of isobutyronitrile and 2 ml of concentrated sulphuric acid are introduced, and the mixture is heated to 70° C. until dissolution has taken place. 4 g (0.0165 mol) of 2-(4-chlorophenyl)-6-methylimidazo[1,2-a]pyridine and 15 ml of acetic acid are then added, and the mixture is heated on a waterbath, the progress of the reaction being observed by thin layer chromatography. When the starting material has almost completely disappeared, the mixture is allowed to cool, and the precipitate which has formed is filtered, taken up with water and ammonia solution and extracted with methylene chloride.

The organic phase is washed with water, dried and evaporated. The residue is purified on a silica column, eluting with a 95:5 methylene chloride/methanol mixture. The compound obtained melts at 211°-212° C.

EXAMPLE 4

2-(4-Chlorophenyl)-3-benzoylaminomethyl-6-methylimidazo[1,2-a]pyridine.

To a solution of 4.54 g (0.03 mol) of N-(hydroxymethyl)benzamide in 50 ml of glacial acetic acid, 2 g of concentrated sulphuric acid are added, and then, after 15 minutes' heating at 50° C., 4.8 g (0.02 mol) of 2-(4-chlorophenyl)-6-methylimidazo[1,2-a]pyridine are added.

The mixture is heated under reflux for 6 hours and then evaporated to dryness. The residue is taken up with water and ammonia solution added until a basic pH is obtained. The precipitate is filtered, washed with water, dried and recrystallised in 400 ml of methanol. White crystals are obtained which melt at 247°–248° C.

EXAMPLE 5

2-(4-chlorophenyl)-3-(2-oxo-1-pyrrolidinylmethyl)-6-methylimidazo[1,2-a]pyridine.

An intimate mixture is prepared of 4.8 g (0.02 mol) of 2-(4-chlorophenyl)-6-methylimidazo[1,2-a]pyridine and 2.53 g (0.022 mol) of N-hydroxymethyl-2-pyrrolidinone, and this is then introduced into 20 ml of concentrated sulphuric acid. The solution is stirred for one day at room temperature, then poured into 800 ml of water, and 55 ml of ammonia solution are added. The lactam is extracted with methylene chloride, the organic phase is washed, dried and evaporated, and the residue is purified by chromatography, eluting with a 70:30 ethyl acetate, toluene mixture. The white solid obtained melts at 186°–187.5° C.

EXAMPLE 6

2-(3,4-dimethylphenyl)-3-[N-(methyl)-3-methyl-butanoylaminomethyl]-6-methyl-imidazo[1,2-a]-pyridine.

6.1. 20.5 g (0.188 mole) of 2-amino-5-methyl pyridine and 32 g (0.381 mole) of NaHCO$_3$ are added to a solution of 42 g (0.188 mole) of 1-(3,4-dimethyl-phenyl)-2-bromoethanone in 400 ml of 95% ethanol. The suspension is heated at reflux temperature for 6 hours, is cooled and is concentrated under reduced pressure. The residue is washed with water, with a mixture of ether/ethanol, with a mixture of ether/acetone and finally with ether. A yellow powder is obtained whose purity is sufficient to continue the synthesis.

M.p.: 157°–160° C.

6.2. 13.5 g (0.057 mole) of imidazopyridine obtained above (6.1.) are dissolved in 80 ml of acetic acid containing 20 ml of 37% formaldehyde in water. The solution is heated at 55° C. for 4 hours and is concentrated under reduced pressure. The residue is taken up with water and is treated with an excess of ammonia until basic pH is reached. The resulting suspension is stirred for 24 hours in the presence of 200 ml of CH$_2$Cl$_2$, the insoluble material is collected by filtration through sintered glass and is washed with water and then with ether and dried.

An amorphous white powder is obtained.

M.p.: 209°–210° C.

6.3. 3.5 ml of concentrated sulfuric acid are added slowly dropwise to a solution of 20 ml isovaleronitrile containing 3.5 g (0.0131 mole) of the alcohol obtained above in 6.2. The mixture is stirred for 1.5 hours at room temperature and then for 2 hours at 110° C. The suspension is cooled, is treated with 100 g of ice and then by an excess of ammonia until basic pH is reached. The insoluble material is extracted with CH$_2$Cl$_2$ and is purified by silica chromatography. The secondary amide (Ia) is obtained, in the form of a viscous oil whose hydrochloride melts at 217°–218° C.

6.4. 3.53 g (0.001 mole) of the secondary amide obtained above in 6.3. in solution in 35 ml of THF are added to a suspension of 1.16 g (0.0024 mole) of NaH (at 50% in oil) in 20 ml of THF containing 1.26 ml, i.e. 2.87 g (0.002 mole), of CH$_3$I. Stirring is maintained for 3 hours. The suspension is treated with 1 ml of methanol and is then concentrated under reduced pressure. The residue is taken up with water, the insoluble material is extracted with CH$_2$Cl$_2$ and is purified by silica chromatography.

Compound (I) is obtained. M.p.: 103°–104° C.

The hydrochloride of the compound melts at 162.5°–163.5° C.

EXAMPLE 7

2-(3,4-dimethylphenyl)-3-(N-methyl)-butanoylaminomethyl)-6-methyl-imidazo[1,2-a]pyridine.

7.1. 6 g (0.022 mole) of the alcohol obtained in 6.2. are suspended in 50 ml of butyronitrile, followed by the slow addition of 6 ml of concentrated H$_2$SO$_4$. The mixture is stirred at room temperature for 1.5 hours and then it is heated at 140° C. for 0.5 hour. After cooling, supernatant is eliminated and the lower phase is treated with ice. After complete dissolution of the gum, the solution is treated with an excess of NH$_4$OH until strongly basic pH. The insoluble is extracted with CH$_2$Cl$_2$ and is purified by recrystallization in a mixture of cyclohexane and ethyl acetate.

The secondary amide (Ia) is obtained, whose hydrochloride melts at 219°–220° C.

7.2. 3.49 g (0.0104 mole) of the amide obtained above in 7.1. are added to a suspension of 1.19 g of NaH (at 50% in oil) in 20 ml of dry THF containing 1.29 ml, i.e. 2.95 g (0.0208 mole) of CH$_3$I. The reaction mixture is diluted with 30 ml of THF. Stirring is maintained for 2 hours, 1 ml of methanol is added and the mixture is concentrated under reduced pressure. The residue is treated with water, the insoluble material is extracted with CH$_2$Cl$_2$ and is purified on silicagel chromatography.

An oil is obtained whose hydrochloride melts at 179°–179.5° C.

The table below shows the structures and melting points of other compounds according to the invention.

TABLE

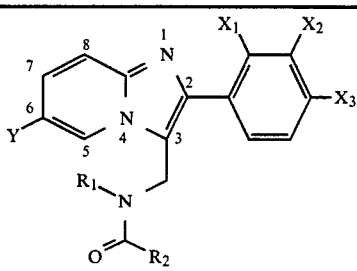
(I)

| Compound | Y | $X_1$ | $X_2$ | $X_3$ | R1 | R2 | m.p. (°C.)-Salt |
|---|---|---|---|---|---|---|---|
| 1 | H | H | H | Cl | H | $CH_3$ | 205–206(b) |
| 2 | H | H | H | $CH_3$ | H | $CH_3$ | 174–175(b) |
| 3 | $CH_3$ | H | H | $CH_3$ | H | $CH_3$ | 218–218,5(b) |
| 4 | $CH_3$ | H | H | Cl | H | $CH_3$ | 230–231(b) |
| 5 | $CH_3$ | H | H | Cl | H | $C_2H_5$ | 190–191(b) |
| 6 (Ex. 3) | $CH_3$ | H | H | Cl | H | $iC_3H_7$ | 211–212(b) |
| 7 | $CH_3$ | H | H | Cl | H | $nC_3H_7$ | 185–187(b) |
| 8 (Ex. 1) | $CH_3$ | H | H | Cl | H | $nC_4H_9$ | 172–173(b) |
| 9 | $CH_3$ | H | H | Cl | H | $iC_4H_9$ | 192–194(b) |
| 10 | $CH_3$ | H | H | Cl | H | $tC_4H_9$ | 226–228(b) |
| 11 (Ex. 4) | $CH_3$ | H | H | Cl | H | $C_6H_5$ | 247–248(b) |
| 12 | $CH_3$ | H | H | H | H | $C_6H_5$ | 209–211(b) |
| 13 | $CH_3$ | H | H | Cl | H | (2-thienyl) | 209–210(b) |
| 14 | $CH_3$ | H | H | $CH_3$ | $CH_3$ | $C_2H_5$ | 151–152(b) |
| 15 | $CH_3$ | H | H | Cl | $CH_3$ | $CH_3$ | 199–200(b) |
| 16 | $CH_3$ | H | H | Cl | $C_2H_5$ | $CH_3$ | 293–294(b) |
| 17 | $CH_3$ | H | H | Cl | $nC_4H_9$ | $CH_3$ | 182–183(b) |
| 18 | $CH_3$ | H | H | Cl | $CH_2C_6H_5$ | $CH_3$ | 149–150(b) |
| 19 | $CH_3$ | H | H | Cl | $CH_3$ | $C_2H_5$ | 210–212(b) |
| 20 | $CH_3$ | H | H | Cl | $CH_3$ | $nC_3H_7$ | 193–195(b) |
| 21 | $CH_3$ | H | H | Cl | $CH_3$ | $iC_3H_7$ | 152–154(b) |
| 22 (Ex. 2) | $CH_3$ | H | H | Cl | $CH_3$ | $nC_4H_9$ | 158–160(b) |
| 23 | $CH_3$ | H | H | Cl | $CH_3$ | $tC_4H_9$ | 160–162(b) |
| 24 | $CH_3$ | H | H | Cl | $CH_3$ | $C_6H_5$ | 198–199(b) |
| 25 (Ex. 5) | $CH_3$ | H | H | Cl | —$(CH_2)_3$— | | 186–187,5(b) |
| 26 | $CH_3$ | H | H | Cl | —$(CH_2)_4$— | | 145–146(b) |
| 27 | $CH_3$ | H | H | Cl | —$(CH_2)_5$— | | 150–151(b) |
| 28 | $CH_3$ | H | H | Cl | $CH_3$ | $iC_4H_9$ | 185–186(b) |
| 29 | $CH_3$ | H | H | Cl | $CH_3$ | $nC_5H_{11}$ | 127–129(b) |
| 30 | $CH_3$ | H | H | Cl | $CH_3$ | (2-thienyl) | 178–180(b) |
| 31 | $CH_3$ | H | H | Cl | $CH_3$ | $nC_6H_{13}$ | 104–105(b) |
| 32 | $CH_3$ | H | H | Cl | $CH_3$ | $CH_2C_6H_5$ | 126–127(b) |
| 33 | $CH_3$ | H | H | Cl | $CH_3$ | $CH=CHCH_3$ | 225–227(b) |
| 34 | $CH_3$ | H | H | $OCH_3$ | $CH_3$ | $nC_3H_7$ | 135–136(b) |
| 35 | $CH_3$ | H | H | $OCH_3$ | $CH_3$ | $iC_4H_9$ | 93–95(b) |
| 36 | $CH_3$ | H | H | $NO_2$ | $CH_3$ | $nC_3H_7$ | 154–156(b) |
| 37 | $CH_3$ | H | H | $NO_2$ | $CH_3$ | $iC_4H_9$ | 157–159(b) |
| 38 | $CH_3$ | H | H | $SO_2CH_3$ | $CH_3$ | $nC_3H_7$ | 182–183(b) |
| 39 | $CH_3$ | H | H | $SO_2CH_3$ | $CH_3$ | $iC_4H_9$ | 120–122(b) |
| 40 | $CH_3$ | H | H | H | $CH_3$ | $nC_3H_7$ | 125–126,5(b) |
| 41 | $CH_3$ | H | H | H | $CH_3$ | $iC_4H_9$ | 154–156(b) |
| 42 | $CH_3$ | H | H | $NHCOCH_3$ | $CH_3$ | $nC_3H_7$ | 110–111(b) |
| 43 | $CH_3$ | H | H | $NHCOCH_3$ | $CH_3$ | $iC_4H_9$ | 183–185(b) |
| 44 | $CH_3$ | H | H | $N(COCH_3)_2$ | $CH_3$ | $nC_3H_7$ | 117–118(b) |
| 45 | $CH_3$ | H | H | $NH_2$ | $CH_3$ | $iC_4H_9$ | 177,5–178,5(b) |
| 46 | $CH_3$ | H | H | $NHCH_3$ | $CH_3$ | $iC_4H_9$ | 176–177(b) |
| 47 | $CH_3$ | H | H | $N(CH_3)_2$ | $CH_3$ | $iC_4H_9$ | 117–118(b) |
| 48 | $CH_3$ | H | H | Cl | $CH_3$ | $4\text{-}Cl\text{-}C_6H_4$ | 175–177(b) |
| 49 | $CH_3$ | H | H | $nC_4H_9$ | $CH_3$ | $iC_4H_9$ | 72,5–73(b) |
| 50 | $CH_3$ | H | H | $C_2H_5$ | $CH_3$ | $iC_4H_9$ | 99–101(b) |
| 51 | $CH_3$ | H | H | $C_2H_5$ | $CH_3$ | $nC_3H_7$ | 108–110(b) |
| 52 | $CH_3$ | H | H | F | $CH_3$ | $iC_4H_9$ | 184–185(b) |
| 53 | $CH_3$ | H | H | F | $CH_3$ | $nC_3H_7$ | 157–158(b) |
| 54 | $CH_3$ | H | H | $SCH_3$ | $CH_3$ | $iC_4H_9$ | 102–104(b) |
| 55 | $CH_3$ | H | H | $SCH_3$ | $CH_3$ | $nC_3H_7$ | 128–129(b) |

TABLE-continued (I)

Structure: pyrido-imidazole system with substituents Y (position 6), X₁, X₂, X₃ on phenyl ring, and side chain -CH₂-N(R₁)-C(=O)-R₂ at position 3.

| Compound | Y | X₁ | X₂ | X₃ | R1 | R2 | m.p. (°C.)-Salt |
|---|---|---|---|---|---|---|---|
| 56 | CH₃ | H | H | CH₃ | CH₃ | iC₄H₉ | 129–131(b) |
| 57 | CH₃ | H | H | CH₃ | CH₃ | nC₃H₇ | 145–147(b) |
| 58 | H | H | H | Cl | CH₃ | iC₄H₉ | 90–91(b) |
| 59 | H | H | H | Cl | CH₃ | nC₃H₇ | 171–173(b) |
| 60 | Cl | H | H | Cl | CH₃ | iC₄H₉ | 176–177(b) |
| 61 | Cl | H | H | Cl | CH₃ | nC₃H₇ | 188–189(b) |
| 62 | Cl | H | H | F | CH₃ | nC₃H₇ | 154–155(b) |
| 63 | Cl | H | H | F | CH₃ | iC₄H₉ | 173–174(b) |
| 64 | Cl | H | H | C₂H₅ | CH₃ | nC₃H₇ | 134–136(b) |
| 65 | Cl | H | H | C₂H₅ | CH₃ | iC₄H₉ | 111–112(b) |
| 66 | Cl | H | H | CH₃ | CH₃ | nC₃H₇ | 164–165(b) |
| 67 | Cl | H | H | CH₃ | CH₃ | iC₄H₉ | 154–155(b) |
| 68 | Cl | H | H | OCH₃ | CH₃ | nC₃H₇ | 152–153(b) |
| 69 | Cl | H | H | OCH₃ | CH₃ | iC₄H₉ | 131–132(b) |
| 70 | Cl | H | H | SCH₃ | CH₃ | nC₃H₇ | 139–141(b) |
| 71 | Cl | H | H | SCH₃ | CH₃ | iC₄H₉ | 135–136(b) |
| 72 | CH₃ | H | H | Cl | H | nC₅H₁₁ | 164–166(b) |
| 73 | CH₃ | H | H | Cl | H | nC₆H₁₃ | 159–161(b) |
| 74 | CH₃ | H | H | Cl | H | CH₂C₆H₅ | 194–195(b) |
| 75 | CH₃ | H | H | Cl | H | CH₂CH=CH₂ | 179–180(b) |
| 76 | CH₃ | H | H | Cl | H | 4-Cl—C₆H₄ | 252–254(b) |
| 77 | CH₃ | H | H | Cl | H | CCl₃ | 228–230(b) |
| 78 | CH₃ | H | H | nC₄H₉ | H | iC₄H₉ | 118,5–119,5(b) |
| 79 | CH₃ | H | H | F | H | iC₄H₉ | 188–190(b) |
| 80 | CH₃ | H | H | F | H | nC₃H₇ | 140–141(b) |
| 81 | CH₃ | H | H | SCH₃ | H | iC₄H₉ | 183–184(b) |
| 82 | CH₃ | H | H | SCH₃ | H | nC₃H₇ | 170–172(b) |
| 83 | CH₃ | H | H | CH₃ | H | iC₄H₉ | 161–162(b) |
| 84 | CH₃ | H | H | CH₃ | H | nC₃H₇ | 170–171(b) |
| 85 | H | H | H | Cl | H | iC₄H₉ | 175–176(b) |
| 86 | H | H | H | Cl | H | nC₃H₇ | 198–199(b) |
| 87 | Cl | H | H | Cl | H | iC₄H₉ | 223,5–224(b) |
| 88 | Cl | H | H | Cl | H | nC₃H₇ | 217–218(b) |
| 89 | CH₃ | H | H | C₂H₅ | H | nC₃H₇ | 150–151(b) |
| 90 | CH₃ | H | H | C₂H₅ | H | iC₄H₉ | 154–155(b) |
| 91 | CH₃ | H | H | OCH₃ | H | nC₃H₇ | 143–144(b) |
| 92 | CH₃ | H | H | OCH₃ | H | iC₄H₉ | 171–172(b) |
| 93 | CH₃ | H | H | SO₂CH₃ | H | nC₃H₇ | 209–211(b) |
| 94 | CH₃ | H | H | SO₂CH₃ | H | iC₄H₉ | 175–176(b) |
| 95 | CH₃ | H | H | NO₂ | H | nC₃H₇ | 210–212(b) |
| 96 | CH₃ | H | H | NO₂ | H | iC₄H₉ | 200–222(b) |
| 97 | CH₃ | H | H | H | H | nC₃H₇ | 155–156(b) |
| 98 | CH₃ | H | H | H | H | iC₄H₉ | (α)137–139(b) (β)168–171(b) |
| 99 | CH₃ | H | H | NHCOCH₃ | H | nC₃H₇ | 204–205(b) |
| 100 | CH₃ | H | H | NHCOCH₃ | H | iC₄H₉ | 183–185(b) |
| 101 | Cl | H | H | F | H | nC₃H₇ | 193–194(b) |
| 102 | Cl | H | H | F | H | iC₄H₉ | 208–209(b) |
| 103 | Cl | H | H | C₂H₅ | H | nC₃H₇ | 181–182(b) |
| 104 | Cl | H | H | C₂H₅ | H | iC₄H₉ | 188–189(b) |
| 105 | Cl | H | H | CH₃ | H | nC₃H₇ | 191–192(b) |
| 106 | Cl | H | H | CH₃ | H | iC₄H₉ | 203–204(b) |
| 107 | Cl | H | H | OCH₃ | H | nC₃H₇ | 183–184(b) |
| 108 | Cl | H | H | OCH₃ | H | iC₄H₉ | 195–196(b) |
| 109 | Cl | H | H | SCH₃ | H | nC₃H₇ | 204–205(b) |
| 110 | Cl | H | H | SCH₃ | H | iC₄H₉ | 207–208(b) |
| 111 | CH₃ | H | H | SCH₃ | nC₃H₇ | iC₄H₉ | 90–91(*) |
| 112 | CH₃ | H | H | SC₂H₅ | H | iC₄H₉ | 149–150(b) |
| 113 | CH₃ | H | H | SC₂H₅ | CH₃ | iC₄H₉ | 118,5–119,5(b) |
| 114 | H | H | H | CH₃ | H | nC₃H₇ | 158–159(b) 247–248(*) |
| 115 | H | H | H | CH₃ | H | iC₄H₉ | 170–171(b) |
| 116 | H | H | H | CH₃ | CH₃ | nC₃H₇ | 115,5–116(b) |
| 117 | H | H | H | CH₃ | CH₃ | iC₄H₉ | 87,5–88,5(b) |
| 118 | H | H | H | SCH₃ | H | nC₃H₇ | 184,5–185,5(b) |
| 119 | H | H | H | SCH₃ | H | iC₄H₉ | 170–170,5(b) |
| 120 | H | H | H | SCH₃ | CH₃ | nC₃H₇ | 125–126(*) |

TABLE-continued (I)

| Compound | Y | $X_1$ | $X_2$ | $X_3$ | R1 | R2 | m.p. (°C.)-Salt |
|---|---|---|---|---|---|---|---|
| 121 | H | H | H | $SCH_3$ | $CH_3$ | $iC_4H_9$ | 101–102(*) |
| 122 | H | H | H | $OCH_3$ | H | $nC_3H_7$ | 169–170(b) |
| 123 | H | H | H | $OCH_3$ | H | $iC_4H_9$ | 157–158(b) |
| 124 | H | H | H | $OCH_3$ | $CH_3$ | $nC_3H_7$ | 102,5–103(b) 131–132(*) |
| 125 | H | H | H | $OCH_3$ | $CH_3$ | $iC_4H_9$ | 117–118(*) |
| 126 | H | H | H | $NO_2$ | H | $nC_3H_7$ | 176,5–177(b) |
| 127 | H | H | H | $NO_2$ | H | $iC_4H_9$ | 198–199(b) |
| 128 | H | H | H | $NO_2$ | $CH_3$ | $nC_3H_7$ | 139,5–140(b) |
| 129 | H | H | H | $NO_2$ | $CH_3$ | $iC_4H_9$ | 110,5–111(b) |
| 130 | H | H | H | $NH_2$ | $CH_3$ | $nC_3H_7$ | 186–187(*) |
| 131 | H | H | H | $NH_2$ | $CH_3$ | $iC_4H_9$ | 174–175(*) |
| 132 | H | H | H | $NHCH_3$ | $CH_3$ | $i-C_4H_9$ | 156–157(*) |
| 133 | H | H | H | $N(CH_3)_2$ | $CH_3$ | $i-C_4H_9$ | 116–118(*) |
| 134 | H | H | H | $NCOCH_3$ \| $CH_3$ | $CH_3$ | $i-C_4H_9$ | 170–171(*) |
| 135 | H | H | H | $NHCH_3$ | $CH_3$ | $n-C_3H_7$ | 184–185(b) 168–169(*) |
| 136 | H | H | H | $N(CH_3)_2$ | $CH_3$ | $n-C_3H_7$ | 125–126(b) 85–87(*) |
| 137 | $CH_3$ | Cl | H | Cl | $CH_3$ | $nC_3H_7$ | 146–147(*) |
| 138 | $CH_3$ | H | Cl | Cl | $CH_3$ | $nC_3H_7$ | 124–125(b) |
| 139 | $CH_3$ | H | Cl | H | $CH_3$ | $nC_3H_7$ | 84–85(b) |
| 140 | $CH_3$ | Cl | H | H | $CH_3$ | $nC_3H_7$ | 185–186(b) |
| 141 | $CH_3$ | H | $CH_3$ | H | $CH_3$ | $nC_3H_7$ | 94,5–95(b) |
| 142 | $CH_3$ | H | $OCH_3$ | H | $CH_3$ | $nC_3H_7$ | 165–166(*) |
| 143 | $CH_3$ | $CH_3$ | H | $CH_3$ | $CH_3$ | $nC_3H_7$ | 129–129,5 |
| 144 (Ex. 7) | $CH_3$ | H | $CH_3$ | $CH_3$ | $CH_3$ | $nC_3H_7$ | 181,5–182(*) |
| 145 | $CH_3$ | $CH_3$ | H | $CH_3$ | $CH_3$ | $iC_4H_9$ | 111–112(*) |
| 146 (Ex. 6) | $CH_3$ | H | $CH_3$ | $CH_3$ | $CH_3$ | $iC_4H_9$ | 162,5–163,5(*) |
| 147 | $CH_3$ | H | $OCH_3$ | $OCH_3$ | $CH_3$ | $nC_3H_7$ | 168–168,5(*) |
| 148 | Cl | H | $CH_3$ | $CH_3$ | $CH_3$ | $nC_3H_7$ | 124,5–125(b) |
| 149 | $CH_3$ | Cl | H | Cl | H | $nC_3H_7$ | 160–161(b) |
| 150 | $CH_3$ | H | Cl | Cl | H | $nC_3H_7$ | 160–161(b) |
| 151 | $CH_3$ | H | Cl | H | H | $nC_3H_7$ | 154–155(b) |
| 152 | $CH_3$ | Cl | H | H | H | $nC_3H_7$ | 178–179(b) |
| 153 | $CH_3$ | H | $CH_3$ | H | H | $nC_3H_7$ | 141–142(b) |
| 154 | $CH_3$ | H | $OCH_3$ | H | H | $nC_3H_7$ | 187,5–188,5(*) |
| 155 | $CH_3$ | $CH_3$ | H | $CH_3$ | H | $nC_3H_7$ | 160–161(b) |
| 156 | $CH_3$ | H | $CH_3$ | $CH_3$ | H | $nC_3H_7$ | 219–220(*) |
| 157 | $CH_3$ | $CH_3$ | H | $CH_3$ | H | $iC_4H_9$ | 166–167(b) |
| 158 | $CH_3$ | H | $CH_3$ | $CH_3$ | H | $iC_4H_9$ | 217–218(*) |
| 159 | $CH_3$ | H | $OCH_3$ | $OCH_3$ | H | $nC_3H_7$ | 200–201(*) |
| 160 | Cl | H | $CH_3$ | $CH_3$ | H | $nC_3H_7$ | 154,5–155(b) |
| 161 | H | H | $CH_3$ | $CH_3$ | H | $nC_3H_7$ | 146,5–147(b) |
| 162 | H | H | $CH_3$ | $CH_3$ | $CH_3$ | $nC_3H_7$ | 136–137(*) |

Notes:
$nC_3H_7$, $nC_4H_9$, $nC_zH_{2z+1}$, and the like, denote linear $C_3$, $C_4$, $C_z$ chains, and the like.
$iC_3H_7$ and $iC_4H_9$ denote isopropyl and isobutyl, respectively.
$tC_4H_9$ denotes tertiobutyl.

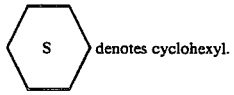 denotes cyclohexyl.

$C_6H_5$ and 4-Cl—$C_6H_4$ denote phenyl and parachlorophenyl, respectively.
(α) and (β): the two melting points correspond to two crystalline modifications.
(b)base
(*)hydrochloride.

The compounds of the invention form the subject of pharmacological experiments which demonstrated their value as substances having therapeutic activities.

Acute toxicity

This was determined in mice, intraperitoneally. The $LD_{50}$ values are greater than 500 mg/kg.

Antagonism towards clonic convulsions induced by Cardiazol ® in mice

The experiment is modelled on the procedure described by Goodman et al., J. Pharm. Exp. Ther., 108, 168–176. The mice received the products to be tested, or the solvent alone, intraperitoneally 30 minutes before the injection of 35 mg/kg of Cardiazol ® intravenously. The animals are then observed for one hour and, for each batch, the percentage of mice showing clonic convulsions is noted (100% of clonic convulsions and 10 to 20% of tonic convulsions in the control animals).

For each dose, the percentage protection relative to the control animals is calculated, and this enables the $AD_{50}$, the dose which protects 50% of the animals as regards the convulsant effects of Cardiazol ®, to be calculated graphically. The $AD_{50}$ values of the compounds of the invention are situated between 0.01 and 30 mg/kg.

"Burying" test in mice

This test is modelled on the method described by Pinel J. P. J., Treit D., Ladak F and MacLennan A. J. in Animal Learning and behaviour, 8, 447–451, (1980).

The presence of foreign bodies in the customary environment of an animal constitutes an aversive situation, to which the animal reacts by burying the subject of the attack (glass balls) in the sawdust in its cage.

Anxiolytic substances have the effect of reducing the apprehension caused by the presence of the foreign bodies: the animals bury less. The number of balls remaining unburied is then counted.

The products to be studied are administered to male CD1 strain mice (Charles River) 30 minutes (intraperitoneally) or 60 minutes (orally) before the latter are placed in cages containing 25 glass balls. After 30 minutes, the number of balls remaining unburied is counted. A percentage is calculated between the treated and control animals.

The $AD_{50}$, 50% active dose, which is the dose of compound (in mg/kg) reducing by one half the number of balls buried, is thus determined, in comparison with the control animals. The $AD_{50}$ values of the compounds of the invention are situated between 0.1 and 30 mg/kg intraperitoneally.

Action on the electrocorticogram of ventilated curarised rats

The sedative or hypnotic activity of the compounds was determined by observing their action on the electrocorticogram of rats according to the method described by H. Depoortere, Rev. E. E. G. Neurophysiol., 10, 3, 207–214 (1980) and by H. Depoortere and M. Decobert, J. Pharmacol. (Paris), 14, 2, 195–265 (1983).

The products to be studied were administered intraperitoneally at doses increasing from 1 to 30 mg/kg. They induce sleep traces from doses ranging from 0.01 to 30 mg/kg.

Effects on the duration of the "sleep" induced by sodium 4-hydroxybutyrate

This action was determined by the influence of a compound on the duration of the "sleep" induced by sodium 4-hydroxybutyrate (GHB) in curarised rats.

The animals used are male Charles River strain rats weighing $200\pm20$ g. The animals, curarised with alloferin in the proportion of 1 mg/kg i.p., are placed under artificial respiration using a mask applied to the muzzle (respiratory frequency=50/minute; respiratory volume=14 ml).

The oesophagus is ligatured beforehand in order to avoid the entry of air into the stomach.

Frontoparietal and occipital cortical electrodes enable the electrocorticographic activity to be recorded on a Grass model 79 P polygraph at a speed of 6 mm/sec.

The preparation of the animal is performed under local anaesthesia (2% strength xylocaine). The rats are maintained throughout the experiment at constant temperature (37.5° C.). Ten minutes after completing the preparation of the rat, a 200 mg/kg dose of sodium 4-hydroxybutyrate is injected intravenously at the tail. A 10 mg/kg dose of the compound to be studied is administered intraperitoneally 3 minutes after the administration of the sodium 4-hydroxybutyrate. Evaluation of the traces in performed in 15-minute periods during 75 minutes after the injection of GHB. During this period of analysis, the total duration of the "sleep" is determined. A series of 15 controls enables the duration of the "GNB sleep" to be precisely defined.

Statistical analysis of the results is carried out by means of the Man-Whitney "U" test.

Some compounds reduce the effects of GHB (up to 40% decrease in the duration of sleep at a dose of 10 mg/kg), while others potentiate these effects (up to 40% increase at a dose of 10 mg/kg). It is also observed that these effects can be opposite, according to whether the compounds are administered at high doses or low doses.

Stress-induced ulcer

The technique used is that of Senay and Levine, Pro. Soc. Exp. Biol. 1967, 124, 1221–1223 and Peptic Ulcers, edited by C. J. PFEIFER, pp. 92–97, on Wistar female rats weighing 120–210 g, fasted for 20 hours and distributed in random groups.

The animals are put under restraint in cylindrical boxes 20 cm×5 cm, and placed in a cold room in which the temperature is maintained at 2°-4° C.

The compounds to be studied are administered orally in the proportion 10, 30 and 100 mg/kg immediately before putting the animals under restraint, the control rats receiving only the placebo.

2 hours later, the animals are sacrified by inhalation of chloroform.

The stomachs are removed and the degree of ulceration noted. The compounds of the invention significantly reduced the stress-induced ulcers.

Analgesic activity

The analgesic activity of the compounds was shown by the "writhing" test described by Koster et al (Fed. Proc., 18, 412, 1959). Fasting mice were administered at 1% in tween 80n, at a dose of 0.2 ml per 20 g of body weight; 30 minutes later acetic acid (a 0.6% solution is a mixture of carboxymethyl-cellulose and Tween 80, at a dose of 10 ml/kg of body weight) is injected intraperitoneally. The number of writhings is counted within 15 minutes.

The percentage of protection is determinated with respect to control animals, and the "effective dose 50 percent" ($ED_{50}$) is calculated graphically.

The $ED_{50}$ of the compounds of the invention is in the range of 5 to 100 mg/kg.

The results of these different tests show that the compounds of the inventions possess anxiolytic, sleep-inducing, hypnotic, anticonvulsant, analgesic and anti-ulcer properties; the compounds of the invention are useful for treating anxiety states, sleep disorders and other neurological and psychiatric conditions, for treating disorders of attentiveness, specially for combatting behavioural disorders which can be ascribed to cerebral vascular damage and cerebral sclerosis in geriatrics, and also for treating absent-mindedness due to cranial trauma, for treating metabolic encephalopathies, and for treating various pains and aches, and stress induced-ulcers.

The compounds of the invention can take any suitalbe form for oral or parenteral administration, for example the form of tablets, dragees, gelatin capsules, solutions to be taken by mouth or injectable solutions, ant the like, in combination with any suitable excipient.

The daily dosage can range from 0.1 to 100 mg.

We claim:

1. Imidazo[1,2-a]pyridine of the formula

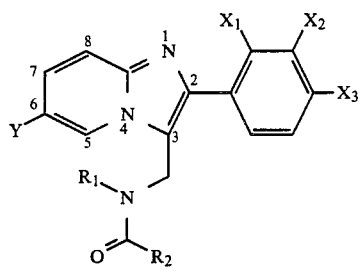

in which each of $X_1$, $X_2$, $X_3$, independently of each other is hydrogen, halogen, $C_1$-$C_4$ alkyl, methoxy, methylthio, ethylthio, methylsulphonyl, nitro, amino, methylamino, dimethylamino, acetylamino and diacetylamino, Y is selected from hydrogen, chlorine and methyl, $R_1$ is selected from hydrogen, $C_1$-$C_4$ alkyl and benzyl, $R_2$ is selected from $C_1$-$C_6$ akyl, cyclohexyl, trichloromethyl, 1-propenyl, allyl, phenyl, 4-chlorophenyl and benzyl, or $R_1$ and $R_2$ together represent a divalent $C_3$-$C_5$ aliphatic group, and their pharmaceutically acceptable acid salts.

2. Compound according to claim 1, wherein at least one of $X_1$, $X_2$ and $X_3$ is selected from chlorine, methyl, methoxy and methylthio, Y is selected from hydrogen, chlorine and methyl, $R_1$ is selected from hydrogen and methyl, and $R_2$ is selected from propyl and isobutyl.

3. An anxiolytic pharmaceutical composition which comprises an effective amount of a compound as claimed in claim 1 in association with a pharmaceutically acceptable excipient.

4. A sleep-inducing or hypnotic pharmaceutical composition which comprises an effective amount of a compound as claimed in claim 1 in association with a pharmaceutically acceptable excipient.

5. An anticonvulsant pharmaceutical composition which comprises an effective amount of a compound as claimed in claim 1 in association with a pharmaceutically acceptable excipient.

6. An analgesic pharmaceutical composition which comprises an effective amount of a compound as claimed in claim 1 in association with a pharmaceutically acceptable excipient.

7. An anti-ulcer pharmaceutical composition which comprises an effective amount of a compound as claimed in claim 1 in association with a pharmaceutically acceptable excipient.

* * * * *